(12) United States Patent
Crabtree et al.

(10) Patent No.: US 7,323,439 B2
(45) Date of Patent: Jan. 29, 2008

(54) METHODS AND COMPOSITIONS FOR MODULATING ANGIOGENESIS

(75) Inventors: Gerald R. Crabtree, Woodside, CA (US); Isabella Graef, Woodside, CA (US); Feng Chen, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 549 days.

(21) Appl. No.: 09/960,708

(22) Filed: Sep. 19, 2001

(65) Prior Publication Data

US 2002/0042360 A1 Apr. 11, 2002

Related U.S. Application Data

(60) Provisional application No. 60/234,694, filed on Sep. 21, 2000.

(51) Int. Cl.
*A61K 31/00* (2006.01)
*A61K 31/70* (2006.01)
*C12N 5/00* (2006.01)

(52) U.S. Cl. .................... 514/1; 514/2; 435/6; 435/7.1; 435/377

(58) Field of Classification Search .................... 514/1, 514/2, 44; 435/6, 7.1, 377
See application file for complete search history.

(56) References Cited

U.S. PATENT DOCUMENTS 6,096,515 A 8/2000 Crabtree et al.

FOREIGN PATENT DOCUMENTS

WO WO 00/30671 6/2000

OTHER PUBLICATIONS

Hernandez et al. "Selective Inhibition of Vascular Endothelial Growth Factor-mediated Angioenesis by Cycloporin A; Roles of the Nuclear Factor of Activated T Cells and Cyclooxygenase 2" *J. Exp Med.*, vol. 193, No. 5, Mar. 5, 2001 pp. 607-620.
Folkman et al "Angiogenesis" *The Journal of Biological Chemistry*, vol. 267, No. 16, Issue of Jun. 5, pp. 10931-10934, 1992.
Clipstone et al. "Identification of calcinerurin as a key signaling enzyme in T-lymphocyte activation" *Nature*, vol. 357, Jun. 25, 1992, pp. 695-697.
Flanagan et al, "Nuclear association of a T-cell transcription factor blocked by FK-506 and cyclosporin A" *Nature*, vol. 352 Aug. 29 1991 pp. 803-807.
Emmel et al. "Cyclosproin A Specifically Inhibits Function of Nuclear Proteins Involved in T Cell Activation" *Science*, vol. 246, Dec. 22, 1989 pp. 1617-1620.
Shaw et al, "Identification of a Putative Regulator of Early T Cell Activation Genes" *Science*, vol. 241, Jul. 8, 1988 pp. 202-205.
Durand et al. "A 275 Basepair fragment at the 5' end of the interleukin 2 gene enhances expression from a heterologous promoter in response to signals from the L cell antigen receptor" *J. Exp. Med* The Rockefeller University Press , col. 165, Feb. 19871 pp. 395-407.
Durand et al, "Characterization of Antigen Receptor Respone Elemetns within the Interleukin-2 Enhancer", *Molecular and Cellular Biology*, Apr. 1988, 0.1715-1724.
Bolontrade et al. "Angiogenesis is an early event in the development of chemically induced skin tumors" *Carcinogenesis* , vol. 19 No. 12 pp. 2107-2113, 1998.
Jiang et al. "Anti-tumor-promoting action of FK506, a potent immunosuppressive agent" *Carcinogenesis*, Jan. 1993, vol. 14, pp. 67-71.
Ranger et al. "The transcription factor NF-Atc is essential for cardiac valve Formation" *Nature*, Mar. 1998, vol. 392, pp. 186-190.
Luis Armesilla et al. "Vascular endothelial growth factor activated nuclear factor of activated T Cells in human endothelial cells: a role for tissue factor gene expression" *Mol. Cell. Biol.* Mar. 1999, vol. 19, No. 3, pp. 2023-2043.

*Primary Examiner*—Sean McGarry
(74) *Attorney, Agent, or Firm*—Bozicevic, Field & Francis LLP; Bret E. Field; David C. Scherer

(57) ABSTRACT

Methods and compositions for modulating angiogenesis in a host are provided. In the subject methods, an effective amount of $Ca^{2+}$/calcineurin/NF-ATc signaling pathway modulatory agent is administered to the host. In many embodiments, the $Ca^{2+}$/calcineurin/NF-ATc signaling pathway modulatory agent is an NF-ATc antagonist, e.g., in those embodiments of inhibiting angiogenesis. The subject methods find use in a variety of different applications, including the inhibition of tumor growth and the treatment of disease conditions characterized by tumor presence. Also provided are methods of screening for agents that inhibit angiogenesis by modulating the $Ca^{2+}$/calcineurin/NF-ATc signaling pathway.

18 Claims, 1 Drawing Sheet

METHODS AND COMPOSITIONS FOR MODULATING ANGIOGENESIS

CROSS REFERENCE TO RELATED APPLICATIONS

Pursuant to 35 U.S.C. § 119 (e), this application claims priority to the filing date of the U.S. Provisional Patent Application Ser. No. 60/234,694 filed Sep. 21, 2000; the disclosures of which are herein incorporated by reference.

INTRODUCTION

1. Field of the Invention

The field of this invention is angiogenesis.

2. Background of the Invention

Angiogenesis or vascular development refers to the growth and development blood vessels, e.g., arteries and veins. There are many physical conditions that would benefit from methods of controlled modulation of angiogenesis or vascular development. For example, agents that promote angiogenesis have potential application in the treatment of conditions where new blood vessel growth is desired, e.g., in the treatment of heart disease conditions characterized by the presence of one or more partially or completely occluded blood vessels. Conversely, agents that inhibit angiogenesis are potentially suitable for use in the treatment of disease conditions characterized by the growth of unwanted new blood vessels. One class of disease conditions falling into this latter category are those characterized by the presence of tumors, particularly vascularized tumors.

The above potential applications for angiogenic modulatory agents has caused a substantial amount of research into the mechanism of angiogenesis to be performed, which research has resulted in the identification of a number of molecules that are involved in angiogenesis. Such compounds include VEGF and its receptors; Ang 1, Tie 2, ephrin-B2; Id1/Id2 and EphB2/EphB3.

Despite the identification of the above molecules as being involved in angiogenesis, there is continued interest in the identification of other molecules that are involved in the growth of blood vessels, as such additional molecules would provide yet more targets for achieving angiogenesis/vascular development modulation.

Relevant Literature

For a description of the $Ca^{2+}$/Calcineurin/NF-AT signaling pathway, see: Durand et al., J. Exp. Med. (1987) 165: 395-407; Durand et al., *Mol. Cell Biol.* (1988) 8:1715-1724; Shaw et al., Science (1988) 241:202-205; Emmel et al., *Science* (1989) 246:1617-1620; Flanagan et al., Nature (1991) 352:803-807; and Clipstone et al., *Nature* (1992) 357:695-697.

For a review of angiogenesis, see Folkman & Shing, J. Biol. Chem. (1992) 267:10931-10934.

Also of interest are: U.S. Pat. Nos. 6,096,515 and WO 00/30671.

SUMMARY OF THE INVENTION

Methods and compositions for modulating angiogenesis in a host are provided. In the subject methods, an effective amount of a $Ca^{2+}$/calcineurin/NF-ATc signaling pathway modulatory agent is administered to the host. In many embodiments, the $Ca^{2+}$/calcineurin/NF-ATc signaling pathway modulatory agent is an NF-ATc antagonist, e.g., in embodiments of inhibiting angiogenesis, and the like. The subject methods find use in a variety of different applications, including the inhibition of tumor growth and the treatment of disease conditions characterized by tumor presence. Also provided are methods of screening for agents that inhibit angiogenesis through modulation of the $Ca^{2+}$/calcineurin/NF-ATc signaling pathway.

DESCRIPTION OF THE SPECIFIC EMBODIMENTS

Figure 1:
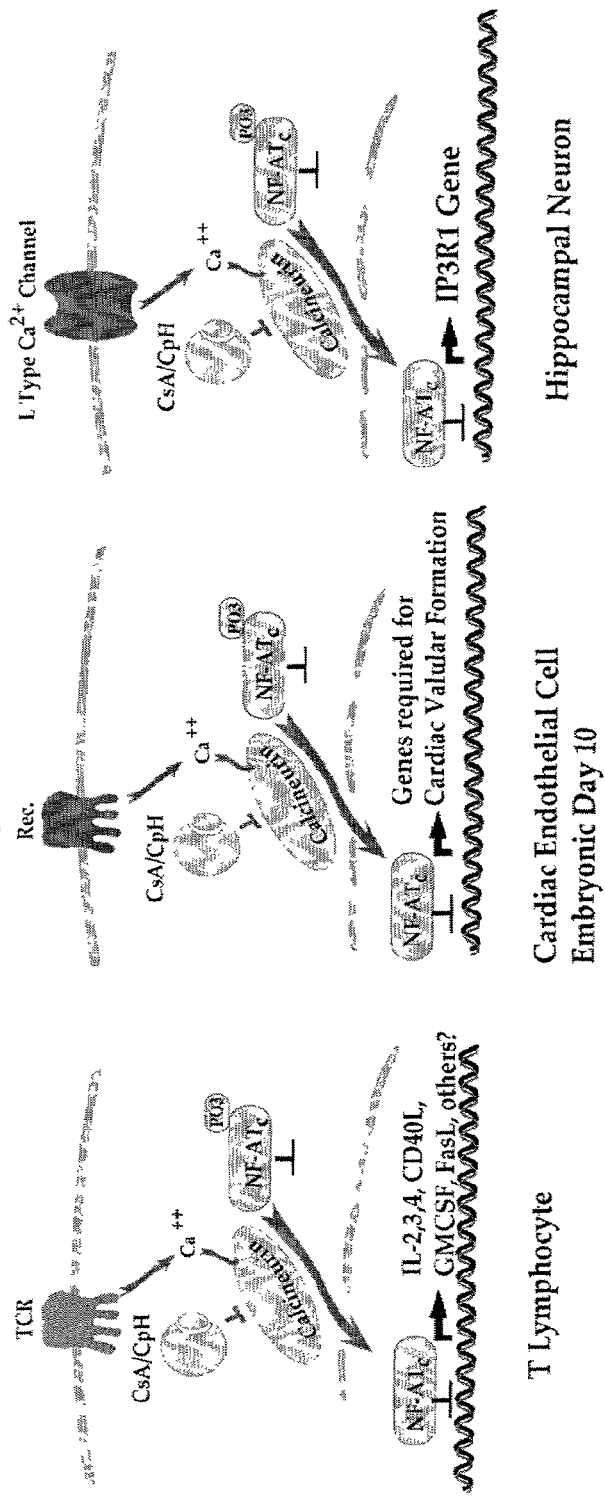
FIG. 1 provides a schematic diagram of the $Ca^{2+}$/calcineurin/NF-ATc signaling pathway.

Methods and compositions for modulating angiogenesis and vascular development in a host are provided. In the subject methods, an effective amount of a $Ca^{2+}$/calcineurin/NF-ATc signaling pathway modulatory agent is administered to the host. In many embodiments, the $Ca^{2+}$/calcineurin/NF-ATc signaling pathway modulatory agent is an NF-ATc antagonist, e.g., in embodiments of inhibiting angiogenesis, and the like. The subject methods find use in a variety of different applications, including the inhibition of tumor growth and the treatment of disease conditions characterized by tumor presence. Also provided are methods of screening for agents that inhibit angiogenesis by modulating the $Ca^{2+}$/calcineurin/NF-ATc signaling pathway.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In addition, many modifications may be made to adapt a particular situation, material, composition of matter, process, process step or steps, to the objective, spirit and scope of the present invention. All such modifications are intended to be within the scope of the claims made herein.

In this specification and the appended claims, the singular forms "a," "an" and "the" include plural reference unless the context clearly dictates otherwise. Conversely, it is contemplated that the claims may be so-drafted to exclude any optional element. This statement is intended to serve as antecedent basis for use of such exclusive terminology as "solely," "only" and the like in connection with the recitation of claim elements or by use of a "negative" limitation Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Also, it is contemplated that any optional feature of the inventive variations described herein may be set forth and claimed independently, or in combination with any one or more of the features described herein.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All existing subject matter mentioned herein (e.g., publications, patents, patent applications and hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

Methods

As summarized above and described in more detail below, the subject invention provides methods of modulating angiogenesis and vascular development in a host. By modulating is meant that the subject methods provide a means for changing, e.g., enhancing, inhibiting, impairing, altering, etc., vascular development in a host, e.g., remodeling, maturation and stabilization of the vascular growth process, as compared to a control. The vascular development modulation may result from one or more different mechanisms. For example, the subject invention may change/influence/alter vascular development through modulation, either directly or indirectly, of the transcription of angiogenic genes in cell, which modulation in turn results in modulation of angiogenesis in a host in which the cell is present. By angiogenic gene is meant a gene that encodes a factor or protein which participates in angiogenesis and/or vascular development, i.e., which is involved in the production or growth of new blood vessels, e.g. through the development and growth of particular cell types, via the recruitment of cells to a particular location, etc. The factor or protein may or may not interact with one or more additional proteins/factors to result in its angiogenic activity. For purposes of this disclosure, a gene is considered to be an angiogenic gene if it encodes a product that is involved at any stage of angiogenesis. Of particular interest, in view of the description provided below, are those angiogenic genes whose expression is modulated by NF-AT transcription factors, particularly NF-ATc transcription factors, e.g., NF-ATc3 and/or NF-ATc4. An angiogenic gene is considered to be modulated by an NF-AT transcription factor if transcription of the gene and therefore expression of the product encoded thereby is, at least partially, dependent on binding of an NF-AT transcription factor to a region of the gene.

A feature of the subject invention is that the desired modulation is achieved through modulation of a $Ca^{2+}$/calcineurin/NF-ATc signaling pathway, which signaling pathway the inventors have discovered to be involved in angiogenesis/vascular development, as demonstrated in the Experimental Section, infra. A schematic of the $Ca^{2+}$/calcineurin/NF-ATc signaling pathway in different cell types is provided in FIG. 1. Modulation of the $Ca^{2+}$/calcineurin/NF-ATc signaling pathway can be achieved using any convenient protocol. Generally, the protocol employs the use of an agent which modulates the $Ca^{2+}$/calcineurin/NF-ATc signaling pathway, i.e., a $Ca^{2+}$/calcineurin/NF-ATc signaling pathway modulatory agent. The modulatory agent may enhance or inhibit the $Ca^{2+}$/calcineurin/NF-ATc signaling pathway, where in many embodiments of the subject invention, the agent inhibits the $Ca^{2+}$/calcineurin/NF-ATc signaling pathway, i.e., the agent is a $Ca^{2+}$/calcineurin/NF-ATc signaling pathway inhibitory agent.

Where the agent is a $Ca^{2+}$/calcineurin/NF-ATc signaling pathway inhibitory agent, the agent may act by interfering or modulating the interaction of any two elements of the pathway, where the modulation results in inhibition of the pathway and, ultimately, a modulation in vascular development in the host. In many embodiments, the agent is an NF-ATc antagonist, by which is meant it is an agent that somehow reduces the NF-ATc activity in the $Ca^{2+}$/calcineurin/NF-ATc signaling pathway. A number of different NF-ATc antagonists may be employed, where representative NF-ATc antagonists include: (1) agents that inhibit calcineurin dephosphorylation of NF-ATc; (2) agents that inhibit nuclear translocation of dephosphorylated NF-ATc (agents that block nuclear import of NF-ATc3 and NF-ATc4; (3) agents that inhibit DNA binding of an NF-ATc-partner protein binding complex, e.g., through binding to a DNA binding portion of NF-ATC and/or the partner protein binding region, including agents that inhibit DNA binding by NF-ATc and agents that prevent the interaction of NF-ATc with their nuclear partner proteins; (4) agents that reduce the amount of intracellular NF-ATc, e.g., agents that inhibit NF-ATc expression; (5) agents that enhance the rate of nuclear export by activating GSK3, PKA or other NFAT kinases; and the like; etc. Each of these types of agents will now be described in greater detail.

As mentioned above, one class of NF-ATc atagonist agents of interest is made up of agents that inhibit calcineurin dephosphorylation of NF-ATc, e.g., by binding to calcineurin's regulatory region or NF-AT interaction domain, etc. Such agents include, but are not limited to: (1) FK506 and rapamycin, as well as synthetic mimetics thereof including those described in U.S. Pat. Nos.: 5,665,774; 5,622,970; 5,516,797; 5,614,547; and 5,403,833, the disclosures of which are herein incorporated by reference; naturally occurring cyclosporins, such as cyclosporin A, as well as synthetic derivatives and mimetics thereof, including those described in U.S. Pat. Nos.: 5,401,649; 5,318,901; 5,236,899; 5,227,467; 5,214,130; 5,122,511; 5,116,816; 5,089,390; 5,079,341; 5,017,597; 4,940,719; 4,914,188; 4,885,276; 4,798,823; 4,771,122; 4,703,033; 4,554,351; 4,396,542; 4,289,851; 4,288,431; 4,220,61 and 4,210,581, the disclosures of which are herein incorporated by reference; etc.

Another class of NF-ATc antagonist agents of interest are agents that inhibit nuclear translocation of NF-ATc. Representative agents of this class of agents are those that bind to NF-ATc translocation sequences in the proteins, and thereby inhibit NF-ATc translocation into the nucleus. Yet another class of NF-ATc antagonist agents of interest are agents that inhibit DNA binding of an NF-ATc-partner protein binding complex, e.g., through binding to a DNA binding portion of NF-ATc and/or the partner protein binding region of NF-ATc. Yet another class of agents of interest are agents that reduce the amount of NF-ATc present in target cells, i.e., cells that express angiogenic factors, where agents of interest include agents that inhibit NF-ATc expression (including antisense, vectors that encode dominant negative mutants of NF-ATc, and the like); etc.

Yet other additional agents of interest include those described in U.S. Pat. No. 6,096,515 and U.S. application Ser. No. 09/198,977; the disclosures of which are herein incorporated by reference; where such agents include polypeptide agents, e.g., NF-ATc proteins and active fragments/portions thereof; nucleic acid agents; e.g., NF-ATc coding sequences, antisense molecules, etc.; antibodies and binding mimetics thereof; and agents identified in NF-ATc signaling pathway screening assays, described therein and in greater detail below.

A variety of different types of molecules may be used as the active agent, where the nature of the molecule employed may depend, at least in part, on the particular molecule with which it interacts within the $Ca^{2+}$/calcineurin/NF-ATc signaling pathway. As such, $Ca^{2+}$/calcineurin/NF-ATc signaling pathway modulatory agents of interest include, but are not limited to: small or low molecular weight compounds, peptides, polypeptides and proteins (including intrabodies); nucleic acids, e.g., antisense molecules, and the like. Of particular interest in many embodiments are small molecule compounds. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, nucleic acids, fatty acids, steroids, purines, pyrimidines, derivatives, structural analogs or combinations thereof.

As mentioned above, the subject invention provides methods of inhibiting angiogenic factor expression in a cell. In such methods, the target cell is contacted with an effective amount of a $Ca^{2+}$/calcineurin/NF-ATc signaling pathway inhibitory agent, where representative agents are described in detail above. The method of contact may vary depending on the location/environment of the target cell and/or the specific nature of the inhibitory agent. For example, where the target cell is present in culture, contact may be achieved by introducing the agent into the culture medium. Alternatively, where the target cell is present in an animal, i.e., in vivo, contact may be achieved through administration of the agent to the animal. By effective amount is meant the amount required to achieve the desired result, i.e., inhibition of angiogenic factor expression, where such amounts may readily be determined empirically.

In addition, the subject invention provides methods of modulating vascular development, e.g., inhibiting or impairing angiogenesis in a host. In these methods, an effective amount of a $Ca^{2+}$/calcineurin/NF-ATc signaling pathway inhibitory agent is administered to the host. By "effective amount" is meant a dosage sufficient to produce the desired result, e.g., an inhibition in angiogenesis, impairment of vascular formation, or an improvement in a disease condition or the symptoms associated therewith associated with or resulting from unwanted angiogenesis. The agent may be administered to the host using any convenient means capable of producing the desired result. Thus, the agent can be incorporated into a variety of formulations for therapeutic administration. More particularly, the agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agent can be achieved in various ways, including oral, buccal, rectal, parenteral, intraperitoneal, intradermal, transdermal, intracheal, etc., administration. In pharmaceutical dosage forms, the agent may be administered alone or in combination with other pharmaceutically active compounds. The following methods and excipients are merely exemplary and are in no way limiting.

For oral preparations, the agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can be utilized in aerosol formulation to be administered via inhalation. The agent can be formulated into pressurized acceptable propellants such as dichlorodifluoromethane, propane, nitrogen and the like.

Furthermore, the agent can be made into suppositories by mixing with a variety of bases such as emulsifying bases or water-soluble bases. The agents can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Utility

The subject methods find use in the treatment of a variety of different disease conditions associated with the presence of unwanted angiogenesis. One disease condition of particular interest is neoplastic deseases, particularly those characterized by the presence of vascularized tumors. By treatment is meant at least an amelioration of the symptoms associated with the disease condition afflicting the host, where amelioration is used in a broad sense to refer to at least a reduction in the magnitude of a parameter, e.g. symptom, associated with the pathological condition being treated, such as size of tumor, rate of growth of tumor, spread of tumor, etc. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition. Another condition that may be treated according to the subject methods is undesired pregnancy, where use of the subject methods can be employed to pharmacologically terminate a pregnancy prior to term, where such applications include animal, particularly mammalian, population control, e.g., to control undesirably large populations of wild animals, domestic animals, etc.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Screening Assays

Also provided are methods of screening a test compound to determine whether it modulates, e.g., enhances or inhibits, angiogenesis. Specifically, methods of screening a test compound to determine whether it inhibits angiogenesis/vascular development mediated by the $Ca^{2+}$/calcineurin/NF-ATc signaling pathway are provided. Generally, the subject screening methods include a step of contacting a test compound with at least two elements of the $Ca^{2+}$/calcineurin/NF-ATc signaling pathway, which elements interact with each other in the absence of the test compound. The $Ca^{2+}$/calcineurin/NF-ATc signaling pathway elements may be entire molecules or portions/derivatives thereof. Representative signaling pathway elements of interest include calcineurin and derivatives thereof, NF-ATc and derivatives/portions thereof; and the like. Following contact of the above described elements, the affect of the test compound on the interaction, e.g., whether the test compound inhibits or enhances the interaction, is then determined. Finally, if the compound does have an effect of the interaction, it is identified as a $Ca^{2+}$/calcineurin/NF-ATc signaling pathway modulatory agent, e.g., an enhancing agent if it enhances the interaction and an inhibitory agent if it inhibits the interaction.

Of particular interest are screening assays that employ calcineurin or a portion thereof to identify agents that inhibit calcineurin's ability to dephosphorylate an NF-ATc. Also of interest are screening assays that employ an NF-ATc, e.g., NF-ATc3 or NF-ATc4, or a portion thereof, to identify agents that inhibit the binding of the NF-ATc protein to its partner protein which is required for DNA binding. Also of interest are screening assays that employ an NF-ATc, e.g., NF-ATc3 or NF-ATc4, or a portion thereof such as the N-terminal portion thereof, to identify agents that inhibit the nuclear translocation of the NF-ATc protein. Also of interest are screening assays that employ an NF-ATc, e.g., NF-ATc3 or NF-ATc4, or a portion thereof, to identify agents that inhibit the transcriptional activation potential of these NF-ATc proteins.

The screening methods of the subject invention may be an in vitro or in vivo format, where both formats are readily developed by those of skill in the art. Depending on the particular method, one or more of, usually one of, the components of the screening assay may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, nucleic acids, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Representative screening assays that can be employed to identify agents that modulate the $Ca^{2+}$/calcineurin/NF-ATc signaling pathway, and therefore agents that modulate the expression of angiogenic factors and angiogenesis mediated by the $Ca^{2+}$/calcineurin/NF-ATc signaling pathway, are also described in U.S. Pat. No. 6,096,515 and U.S. patent application Ser. No. 09/198,977; the disclosures of which are herein incorporated by reference.

EXPERIMENTAL

The following examples are offered by way of illustration and not by way of limitation.

I. Signals Transduced by $Ca^{2+}$ and Calcineurin are Required for Vascular Development

A. Methods

Generation of the CnB Mutant Mice

A targeting vector was designed to replace the stop codon of the ubiquitously expressed CnB with the FRB* tag. The targeting vector was linearized and electroporated into ES (embryonic stem) cells. After double selection, surviving ES clones were screened by western analysis with the anti-CnB antibody (Sigma, 1:3000). One ES clone out of 68 clones screened showed a 29 kD band in addition to the 19 kD band for the endogenous CnB. The 29 kD band was also immunoreactive to an antibody against FRB*. This clone was confirmed to be correctly targeted by southern analysis and long-range genomic PCR. Genotyping of mice was done by PCR, western and southern analyses.

Immunohistochemistry

For whole-mount studies, embryos were processed as described in Suri, C. et al. Requisite role of angiopoietin-1, a ligand for the TIE2 receptor, during embryonic angiogenesis. *Cell* 87, 1171-1180 (1996). Antibodies used are: a rat anti-PECAM-1 monoclonal antibody (Pharmingen, 1:100 dilution), a mouse anti-α smooth muscle actin monoclonal antibody (Sigma, 1:400 dilution). For section staining, embryos were fixed in 10% formalin overnight, processed according to standard protocol. Seven micrometer thick paraffin sections were microwaved twice for 5 minutes each in antigen unmasking solution (Vector Laboratories) and stained with the anti-α smooth muscle actin antibody (Sigma, 1:400 dilution). Electron microscopic analysis was carried out essentially as described in Suri et al., supra.

Immunofluorecence

Paraffin sections were collected and antigen retrieval was done as described above. These sections were subsequently stained with the 7A6 anti-NF-ATc1 antibody (Northrop, J. P. et al. NF-AT components define a family of transcription factors targeted in T-cell activation. *Nature* 369, 497-502 (1994)) (1:400 dilution), using the M.O.M kit (Vector Laboratories). Streptavidin-Alexa-488 was used instead of the Avidin-fluorecein provided with the kit. Images were collected with a deconvolution microscope (DeltaVision, at Stanford Cell Imaging Facility).

Immunoprecipitation 150 ug brain extract from a CnB+/* mouse was incubated overnight at 4° C. with protein A sepharose beads (Pharmacia) and one of the following antibodies, anti-CnB (Sigma 1.5 ul), Anti-CnA (Sigma, 4.5 ul) and anti-HA (1.5 ul) in 10% glycerol, 20 mM Hepes pH7.9, 0.1M KCl, 0.2 mM EDTA, 0.05% NP-40, 0.1 mM DTT. Beads were then washed with 20 mM Hepes pH7.9, 0.1M KCl, 0.2 mM EDTA, 0.05% NP-40, 0.5 mM DTT three times. About one fourth of the washed beads were boiled in standard loading buffer and loaded into a 15% Polyacrymide gel for western analysis with the anti-CnB antibody (1:3000).

B. Results and Discussion

A mouse strain was generated in which the function of calcineurin as a dimeric phosphatase was disrupted. This was accomplished in the course of other studies by adding a FRB* tag to the C-terminus of the ubiquitously expressed CnB. This modification prevented the interaction of CnB with CnA and hence specifically interfered with the $Ca^{2+}$-dependent activation of CnA catalytic activity. The basis of this disruption is evident from the X-ray structure of the CnA-CnB complex in which the C-terminus of CnB has extensive interactions with residues 345 to 420 of the A chain. The FRB* tag was fused to the last codon of CnB gene by homologous recombination in ES cells. The resultant heterozygous (CnB+/*) mice were found to have both the predicted DNA rearrangement and the expected increase in size of the CnB subunit. In addition, antibodies to the FRB* tag also detected the slower migrating band indicating that the CnB-FRB* fusion was in correct reading frame. In embryo extracts, the protein from the mutated allele was expressed at near wild-type levels demonstrating that the fusion did not destablize the CnB* mRNA or protein. To determine if the allele containing the insertion could interact with, and thus activate CnA phosphatase activity, we assayed the ability of CnA to interact with the mutated CnB in brain extracts from CnB+/* mice where the wild-type protein served as an internal control. When calcineurin complexes were immunoprecipitated with CnA antibodies and blotted with an anti-CnB antibody, no detectable interaction with the mutated CnB protein was detected.

CnB+/* mice were indistinguishable from wild-type littermates and have been followed for 4 generations over 14 months with no detectable abnormalities. These results indicate that the FRB* tag on the CnB protein did not have a dominant negative effect on calcineurin function, nor was it likely to be a gain-of-function allele. CnB*/* mice were indistinguishable from wild-type littermates at E8.5 (n=13), except in rare cases in which the pericardial sacs of the CnB*/* embryos were slightly enlarged (data not shown). At E9.5, most CnB*/* embryos (n=51) were alive, but smaller than their littermates to various degrees. The number of their somites pairs, however, was only reduced by 1 to 2. One third of them have significantly enlarged pericardial sacs. Most of them appeared pale but blood filled vessels or sacs were still visible. Proper angiogenesis of the yolk sac vasculature of CnB*/* embryos never occurred resulting in a primary vascular plexus lacking the vitelline vessels. These defects became more severe at E10.5 (n=22) at which point half of the CnB*/* embryos showed no sign of cardiac contraction. Some CnB*/* embryos showed leakage of blood into the pericardial sac and other cavities. The lumena of the yolk sac vasculature were greatly expanded. All E11.5, CnB*/* embryos (n=8) were dead and undergoing reabsorbtion. Whole-mount PECAM staining showed that the primary vasculature was formed in CnB*/* embryos, indicating that vasculogenesis could proceed in the absence of calcineurin function. This primary vascular network, however, failed to remodel into the highly organized branching pattern of the wild-type vasculature. The vessels in the head and the intersomitic vessels followed irregular courses that may be an indication of defective sprouting angiogenesis or an inability to respond to guidance cues. The vessels often had irregular walls and minor aneurysmal dilations. In addition, detachment of the endocardium from the underlying mesenchyme was observed in some CnB*/* embryos, possibly as a result of a weak endothelium-mesenchyme interaction.

The formation of blood vessels requires the recruitment and organization of pericytes and vascular smooth muscle cells (VSMC) around the vascular endothelium. The VSMCs around the dorsal aorta of CnB*/*embryos were disorganized. Rather than forming a continuous tube as in heterozygous or wild-type littermates, the layer of VSMCs was irregular and absent in some areas. Electron microscopic analysis showed that supporting cells, especially the myosin containing VSMCs, were scarce around major vessels. In addition, the endothelial lining of the lumen was discontinous in places, explaining the frequently observed hemorrhage in CnB*/*embryos. These defects appeared similar to but more severe than the defects found in the NF-ATc3$^{-/-}$c4$^{-/-}$ embryos (see accompanying manuscript) suggesting that perhaps other NF-ATc family members or other calcineurin substrates contribute to the phenotype.

In vitro experiments and assays with calcineurin inhibitors indicated that the dephosphorylation of NF-ATc by calcineurin sends these transcription factors to the nucleus. The CnB*/* mice, however, provided the first opportunity to genetically examine this in vivo. By immunostaining with the anti-NF-ATc1 antibody, we showed that endocardial cells of wild-type embryos express NF-ATc1 at E9.5 and the protein is nuclear in the majority of cells. NF-ATc1, however, is excluded from the nucleus of every endocardial cell examined from 6 different CnB*/* embryos. Thus, under physiological conditions calcineurin is indeed necessary for the nuclear localization of NF-ATc1 in endocardial cells as predicted from studies using the inhibitors FK506 and CsA. This experiment also indicated that calcineurin phosphatase activity is defective in the CnB*/* mice.

Since defects in the development of the placenta can lead to abnormalities of the vascular system, we examined the placenta of the CnB*/*embryos. Differentiation of the trophoblast giant cells and the syncytiotrophoblasts appeared normal in the CnB*/* embryos. The organization of the placental layers, including the spongiotrophoblast layer, the labyrinthine trophoblast layer and the labyrinthine layers, was also normal in the mutants. As would be expected from a primary defect in embryonic angiogenesis, there was a minor reduction of vessel complexity on the embryonic side of the placenta. However, there were no defects in the maternal response to the embryo as judged by the decidual response or the degree of maternal vascularization. This data along with the observation of occasional defects in CnB*/*embryos at E8.5, before the placenta is essential, indicated that minor reduction of vessel complexity is unlikely to be the cause of vascular abnormalities in the CnB*/*embryos.

Because CsA is a fast-acting and specific inhibitor of calcineurin, injection of CsA to pregnant mice may reproduce the developmental defects seen in CnB*/* embryos. We subcutaneously injected CsA at 25 mg/kg twice daily to mothers from E6.5 to E9.5 or from E7.5 to E9.5. PECAM staining of the E10.5 embryos taken from these mothers indicated that while endothelial cells did differentiate, there was a failure of vascular development with defects very similar to those of the CnB*/*embryos. To further narrow the window in which calcineurin function is critical in vascular development, we administrated CsA twice daily. E10.5 embryos taken from mothers treated with CsA for only one day between E7.5 and E8.5, but not before or after this period showed severe vascular abnormalities that were essentially equivalent to those seen in the CnB*/*embryos. This study also indicated that inhibitors of calcineurin may be useful in cancer therapies based on the blockage of tumor angiogenesis.

Vasculogenesis, the formation of the primary endothelial network was not noticeably affected in the CnB*/*embryos. Rather, the CnB*/*embryos showed defects in vascular development that were similar to those caused by inactivation of a group of endothelial cell specific receptors and their ligands as well as genes in the TGFβ and BMP pathways. For example, both sprouting angiogenesis and intussusception appeared to be defective in the CnB*/*embryos and in their yolk sacs. Absence of pruning of the primary capillary network to form the continuum of large and small vessels is especially evident in the mutant yolk sacs. These defects and the lack of condensation of VSMCs and other supporting cells in CnB*/* embryos are all characteristic of this group of mutants, especially in mice with mutations in angiopoietin-1 (ang-1) and its receptor Tie2, which play crucial roles in controlling endothelium-mesenchyme interactions. In addition, defective mesenchyme support of vessel formation was described in the Smad5$^{-/-}$ mice, which also have an attenuated VSMC layer. Some of these steps in angiogenesis occur later than the E7.5 to E8.5 window we have defined for critical calcineurin function in vascular development. One explanation for this apparent discrepancy could be that the biochemical events required to initiate angiogenesis precede the morphologic changes, which only become visible in the developing vasculature at E8.5 to E9.5.

There was a 2.5-fold increase of VEGF-A mRNA in CnB*/*embryos by E9.5. The overexpression of VEGF-A may contribute to the vascular defects seen in CnB*/*embryos, since VEGF is one of the most potent mitogens for vascular endothelial cells. This increase in VEGF-A expression, however, is unlikely to be a direct result of the loss of calcineurin/NF-ATc signaling.

Our studies identify calcineurin as an essential signaling molecule in vascular development and provide in vivo genetic evidence that calcineurin controls NF-ATc localization. In addition, since mice doubly mutant for NF-ATc3 and c4 have similar defects, it is likely that the essential functions of calcineurin during development are mediated largely by NF-ATc family members.

II. Control of Vascular Development by $Ca^{2+}$/Calcineurin and NF-ATc3/c4

A. Materials and Methods

Generation of NF-ATc4 Knock-out Mice

Two genomic clones encompassing the entire NF-ATc4 gene were isolated from a genomic 129/Sv library (Stratagene). A 3.0 kb base pair BamHI/BamHI (5' arm) and a 4.4-kilobase pair SacI/SacI (3' arm) fragment were used to construct the targeting vector. The targeting construct deletes exon 1, exon 2 and part of exon 3, coding for amino acid 1 through amino acid 438 of the NFATc4 protein. 288 double-resistant clones were isolated and screened for homologous recombinants by Southern blots. Southern blot analysis of EcoRV digested genomic DNA was carried out using a 5' external and a 3' external probe. NFATc4$^{-/-}$ mice were established by mating of the heterozygotes. Double knock-out mice were generated by intercrossing of 129/Sv/Ev/Tc NFATc4$^{-/-}$ mice with Balb/c NFATc3$^{-/-}$ mice (Oukka, M. et al. The transcription factor NFAT4 is involved in the generation and survival of T cells. *Immunity* 9, 295-304 (1998)).

Western Blots

A rabbit polyclonal antibody against a GST-fusion protein of amino acid 70-245 of human NF-ATc4 was generated. Whole cells RIPA lysates of E10.5 embryos were analyzed by SDS page and Western blot with the polyclonal antibody specific for NF-ATc4.

Morphological and Histological Analysis

Embryos were obtained from timed pregnancies with the noon of the plug date defined as E0.5. Embryos were fixed in Formalin and embedded in paraffin. Sections of 7 μm were stained with hematoxylin and eosin. Electron microscopy was performed as previously described (Sato, T. N. et al. Distinct roles of the receptor tyrosine kinases Tie-1 and Tie-2 in blood vessel formation. *Nature* 376, 70-74 (1995)).

In Situ Hybridization

Whole-mount in situ hybridization with a digoxigenin-labelled riboprobe was performed as previously described (Wilkinson, D. G., Bhatt, S., Cook, M., Boncinelli, E. & Krumlauf, R. Segmental expression of Hox-2 homeobox-containing genes in the developing mouse hindbrain. *Nature* 341, 405-409 (1989)). The NF-ATc4 probe used was generated by PCR and contains bp 2751-3155 of the 3' untranslated region of the murine NF-ATc4 gene.

Whole-mount Immunohistochemistry

Whole-mount immunohistochemistry with the anti-PECAM antibody (clone MEC 13.3, Pharmingen), anti-Flk-1 antibody (clone Avas 12α1, Pharmingen) and anti-smooth muscle actin antibody (clone 1A4, Sigma) was done as described in Schlaeger, T. M., Qin, Y., Fujiwara, Y., Magram, J. & Sato, T. N. Vascular endothelial cell lineage-specific promoter in transgenic mice. *Development* 121, 1089-1098 (1995).

Immunohistochemistry

For immunohistochemistry 7 µm sections were incubated with anti-PECAM-1 antibody, anti-smooth muscle actin antibody (clone 1A4, Sigma), anti Ki-67 antibody (clone B56 Pharmingen).

RNAse Protection Assays

RPA assays were done following standard protocols. The multi-probe template sets were purchased from Pharmingen. The NFATc4 probe was an EcoRI/BamHI fragment containing part of exon 2 of the murine NF-ATc4 gene. All RPA assays were quantified by analysis on a phosphoimager.

CsA Treatment of Pregnant Females

Timed pregnant CD-1 and C57B1/6×C3H F1 females were injected subcutaneously at either E6.5-9.5 or E 7.5-9.5 with 25 mg/kg CsA (Bedford Laboratories) diluted in sterile saline solution twice daily, in the morning and in the evening. The concentration of CsA in mice injected with 25 mg/kg was 2.45 µg/ml of whole blood three hours after injection. For the three hour timepoint, pregnant females were injected with 50 mg/kg CsA at E10.5. Three hours after the 50 mg/kg injection the concentration of CsA in maternal blood was 5.15 µg/ml of whole blood and the CsA concentration in the embryos was 1.94 µg/ml of embryo extract. Embryos were harvested at E10.5.

B. Results and Discussion

NF-ATc4 is one of four genes that encode the $Ca^{2+}$/calcineurin dependent subunits of NF-AT transcription complexes. We disrupted the NF-ATc4 gene by homologous recombination, removing the translational start site, the regulatory domain that controls the calcineurin-dependent cytoplasmic-to-nuclear translocation and part of the DNA binding domain. Southern blot analysis confirmed germline transmission of the targeted allele. No mRNA or protein can be detected in NF-ATc4$^{-/-}$ tissue indicating that these animals bear a null mutation. NF-ATc4$^{-/-}$ mice (observation period 27 months) were viable and fertile and showed no major macroscopic or microscopic abnormalities. NF-ATc4 is widely expressed in early embryos with pronounced expression in the head fold and somites at E8.5 and in the developing neural tube, somites, otic vesicle, pharyngeal arches and limb buds at E9.5 and E10.5. This pattern of expression significantly overlaps with that of NF-ATc3, which is the closest homologue of NF-ATc4, suggesting that the two genes might have some redundant function. Hence, we generated double knock-out mice by crossing the NF-ATc4$^{-/-}$ mice with NF-ATc3$^{-/-}$ mice.

Only 2% of NF-ATc3$^{-/-}$c4$^{-/-}$ mice born from NFATc3$^{+/-}$c4$^{-/-}$ matings (n=395) survived to birth and 50% of these NF-ATc3/c4 null mice were found dead as newborns, the remaining mice were severely runted and died shortly afterwards. To determine the onset of embryonic lethality, we isolated embryos at various stages of gestation and found that NF-ATc3/c4 null embryos died in utero around E11.5 (n=32). At E 9.5 (n=58) the NF-ATc3$^{-/-}$c4$^{-/-}$ embryos exhibited no major morphological defects. At E10.5 (n=216) the NF-ATc3$^{-/-}$c4$^{-/-}$ mice were alive but smaller and anemic, with enlarged pericardial sacs and showed an underdeveloped yolk sac vasculature. The absence of organized vessels in the yolk sac was confirmed by PECAM staining which showed an enlarged and disordered capillary plexus and poorly developed vitelline vessels. Closer examination of the yolk sac vasculature by electron microscopy revealed the absence of pericytes in the mesothelial layer and defective formation or disintegration of contacts between endodermal and mesothelial layers. We sometimes observed the presence of blood in the exocoelomic cavity suggesting that the anemia seen in the embryos might be caused by extravasation of blood from the abnormal yolk sac vessels. Additionally, differentiation of E8.5 and E10.5 NF-ATc3$^{-/-}$c4$^{-/-}$ hematopoietic precursors into erythroid and myeloid lineages in vitro appeared to be normal and expression of early hematopoietic markers such as GATA-1 was comparable to littermates (data not shown). Since growth retardation, defects in vascularization and embryonic lethality can be secondary to defects in the development of the placenta we examined the placenta of the NF-ATc3$^{-/-c}$4$^{-/-}$ embryos. Histological examination of the mutant placentas showed that all cell layers were developed.

At E 9.5, the vasculature of NFATc3$^{+/-}$c4$^{-/-}$ and NF-ATc3$^{-/-}$c4$^{-/-}$ embryos was similar. However, at E10.5 the vascular development of NF-ATc3$^{-/-}$c4$^{-/-}$ embryos was severely abnormal. We used both PECAM and Flk-1 staining to visualize the vasculature in E10.5 embryos. Both whole mount stains showed that, although there was sprouting and branching of the initial vascular plexus, the major vessels including the dorsal aorta, intersomitic vessels, branchial arch arteries and cranial vessels were severely disorganized. The formation and proliferation of endothelial cells was not affected by the absence of NFATc3/c4 as the expression of endothelial markers such as PECAM, Flk-1, Tie-1 and Tie-2 was normal. This indicated that NFATc3/c4 are not required for vasculogenesis but are required for remodeling of the initial vascular plexus and the ability of the developing vasculature to respond to guidance cues.

Microscopically, both arteries and veins were affected and showed thin vessel walls lined by endothelial cells. We also observed breaks in the wall of major vessels and extravasation of erythrocytes into the surrounding tissue suggesting a failure to complete the formation of a stable vessel wall. When we analysed the blood vessels by electron microscopy, we found that ultrastructurally the endothelial cells lining the major vessels appeared normal. Consistent with the light microscopic analysis, there was a marked reduction of pericytes and vascular smooth muscle cells surrounding the aorta and discontinuities of the vascular wall. The fragility of the vessels seemed to be caused by a defect in the assembly of perivascular supporting cells and resultant hypoplasia of the vascular wall.

A critical stage of angiogenesis is the recruitment and differentiation of mesenchymal cells into pericytes and vascular smooth muscle cells to form a stable vascular wall. This process is dependent upon reciprocal signaling between endothelial cells and mesenchymal cells and is thought to involve angiopoietins and their receptors, Tie1 and Tie 2, as well as Flt-1, PDGF-B, tissue factor, the TGF-β pathway and the transcription factor MEF2C. To test whether NFATc3/c4 were critical for this step in angiogenesis, we examined the expression of smooth-muscle actin in the mutant embryos. Whole mounts stains of NFATc3$^{-/-}$c4$^{-/-}$ E10.5 embryos showed poor association of smooth-muscle actin positive cells with the aortic wall, a lack of smooth-muscle cells around the carotid artery and irregular dilations of the aorta, while the somites appeared normal. Staining of sections revealed that the developing vessels of NF-ATc3$^{-/-}$c4$^{-/-}$ embryos had far fewer cells expressing smooth-muscle actin and these cells were usually distributed in the space around the vessel rather than directly adjacent to the vessel, consistent with the defects seen by electron microscopy. The reduction of supporting cells could not be attributed to an increase of apoptosis or a defect in cell proliferation as we did not observe any differences between double mutant embryos and their littermates in Tunel assays or immunostains for Ki-67, a nuclear antigen expressed in proliferating cells. These observations indicated that NF-ATc3/c4 were required for the recruitment of vascular smooth-muscle cell and pericyte precursors to the developing vessel wall. NF-AT-dependent transcription has been reported in both endothelial and smooth muscle cells and NFATc3/c4 have been shown to be involved in muscle differentiation. Since we could not observe distinct expression of NF-ATc3/c4 in the developing vasculature we feel that the primary defect might lie within the perivascular mesenchymal rather than the endothelial compartment.

To precisely determine the level of expression of several genes critical to angiogenesis in the NF-ATc3/c4 null embryos we used multitemplate ribonuclease protection assays. We found that surprisingly all of the genes assayed with the exception of VEGF-A were expressed at normal levels. VEGF-A was overexpressed by 2- to 4-fold in NF-ATc3/c4 null embryos. Since ephrins and their receptors also play critical roles in vascular development, we assayed the expression of the all ephrins and Eph-receptors that are important in angiogenesis. Again these were expressed at normal levels. Similarly, tissue factor, which has been shown to be regulated by NF-ATc2-dependent transcription in response to VEGF signaling, was expressed at normal levels. Thus, in the absence of NF-ATc3/c4, several of the major vascular growth and differentiation factors and receptors were expressed normally. This indicates that the vascular defect observed in the NF-ATc3/c4 null embryos is unlikely due to a failure of transcriptional regulation of any of these genes. However, it is possible that NFATc3/c4 are regulated by signaling via one of the growth factors assayed, which have been shown to be critical for the recruitment of perivascular supporting cells.

The Ca$^{2+}$/calmodulin-dependent phosphatase calcineurin dephosphorylates NF-ATc family members, unmasking their nuclear localization sequences and leading to nuclear import. If NF-ATc3/c4 were functioning in a signaling pathway downstream of Ca$^{2+}$ and calcineurin in embryonic vascular development, one would expect that cyclosporin (CsA) treatment, which inhibits calcineurin, or mutations in calcineurin would reproduce the phenotype seen in the NF-ATc3/c4 null embryos. This is, in fact, the case. Mutation of calcineurin B (CnB$^{*/*}$) as well as administration of CsA to pregnant mice between E7.5 and E8.5 of gestation phenocopied the defects seen in the NF-ATc3$^{-/-}$c4$^{-/-}$ embryos. The defects seen in the NF-ATc3$^{-/-}$c4$^{-/-}$ embryos appeared somewhat less severe than the defect observed in the CnB$^{*/*}$ embryos. While issues such as precise genetic background must be considered, it seems more likely that the differences observed could be due to partial functional redundancy with NFATc1/c2, which are also expressed in early embryos. We examined VEGF-A mRNA expression in CnB$^{*/*}$ embryos (see accompanying manuscript) or in mice treated with CsA for defined periods. Similar to the NF-ATc3$^{-/-}$c4$^{-/-}$ embryos, mice homozygous for the CnB$^{*/*}$ mutation as well as embryos treated between either E6.5-9.5 or E7.5-9.5 showed selective overexpression of VEGF-A with normal expression of the other genes assayed. However, a three hour period of CsA administration followed by immediate measurement of VEGF-A levels did not lead to overexpression of the VEGF-A gene, indicating that NFATc3/c4 may not act as direct repressors of VEGF-A transcription. The observed increase in VEGF-A mRNA could be caused by hypoxia secondary to the vascular defect, since hypoxia induces VEGF-A expression. However, in E9.5 NF-ATc3$^{-/-}$c4$^{-/-}$ embryos, at a stage when there was no apparent vascular defect, we also found overexpression of VEGF-A mRNA. Therefore, it is possible that NF-ATc3/c4 might be necessary for the activation of a subset of VEGF-A-responsive genes and the overexpression of VEGF-A is compensatory response secondary to a reduction of VEGF-A signaling. We conclude that calcineurin functions between E7.5 and 8.5 in a signaling pathway upstream of NF-ATc3/c4 which controls remodeling, maturation and stabilization of the developing vasculature.

III. Small Molecule Inhibitors of Angiogenesis

To determine the time during development when calcineurin signaling is essential, we made use of the highly specific, rapidly acting and reversible inhibitor of calcineurin phosphatase activity, cyclosporin A. Injection of CsA into pregnant mice between days 7.5 and 8.5 but not earlier or later reproduced the vascular developmental defects seen in CnB$^{*/*}$ and c3/c4 null embryos. These embryonic CsA levels completely blocked the ability of calcineurin to dephosphorylate embryonic NFATc4, assayed by Western blots of whole embryo extracts. Similar results were obtained with FK506. PECAM staining of E10.5 embryos taken from these mothers indicated that while endothelial cells did differentiate, there was a failure of vascular organization with defects similar to those of the CnB$^{*/*}$ embryos. The temporally selective action of CsA could not be due to degradation of the drug, failure of placental transfer, or embryonic metabolism of the drugs, since similar levels of CsA were achieved during the critical period and after it. In addition, we found that even at the time that CsA administration had no developmental effect, it still produced hyperphosphorylation of NFATc4, indicating that the drug effectively gained access to the embryo and blocked calcineurin activity. The observation that CsA administration mimics the phenotype of the CnB$^{*/*}$ mutants indicates that in early mammalian development, CsA is a highly specific inhibitor of calcineurin function and is unlikely to have other developmentally critical targets. The above results also indicate that calcineurin phosphatase activity is essential between E7.5 and E8.5 for vascular development. Finally, since developmental mechanisms of angiogenesis in embryos are parallel to those that operate during tumor angiogenesis, the above results indicate that CsA and other inhibitors of calcineurin phosphatase activity are effective tumor angiogenesis inhibitors.

Our studies define a step in vascular development that can be approached pharmacologically. In general, factors known to regulate embryonic angiogenesis also regulate angiogenesis under pathological conditions in the adult. These studies indicate that NF-ATc3/c4 is a molecular target for anti-angiogenic therapy.

It is evident from the above results and discussion that the subject invention provides an important new way to inhibit angiogenesis. By identifying the $Ca^{2+}$/calcineurin/NF-ATc signaling pathway as being involved in angiogenesis and vascular development, the subject invention provides for an important new way to inhibit angiogenesis, i.e., through use of compounds which modulate the $Ca^{2+}$/calcineurin/NF-ATc signaling pathway. As many such compounds are already known and additional compounds may be readily identified using the subject screening protocols, this invention greatly increases the number of active agents that may be employed to inhibit angiogenesis. The subject methods may find use in a variety of different applications, particularly in the treatment of disease conditions characterized by the presence of unwanted angiogenesis, e.g., neoplastic diseases characterized by the presence of tumors. As such, the subject invention represents an important contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of inhibiting angiogenesis/vascular development in a host having a condition associated with unwanted anglogenesis, said method comprising:
   systemically administering to said host an effective amount of a Ca2+/calcineurin/NF-ATc inhibitory agent to inhibit angiogenesis/vascular development in said host-having a condition associated with unwanted angiogenesis.

2. The method according to claim 1, wherein said agent is an NF-ATc antagonist.

3. The method according to claim 2, wherein said agent inhibits phosphorylation of NF-ATc.

4. The method according to claim 3, wherein said agent inhibits NF-ATc phosphorylation by binding to calcineurin.

5. A method of inhibiting tumor growth in a host having a neoplastic disease condition, said method comprising:
   systemically administering to said host having a neoplastic disease condition an effective amount of a Ca2+/calcineurin/NF-ATc inhibitory agent to inhibit tumor growth in said host.

6. The method according to claim 5, wherein said agent is an NF-ATc antagonist.

7. The method according to claim 6, wherein said agent inhibits phosphorylation of NF-ATc.

8. The method according to claim 6, wherein said agent inhibits NF-ATc phosphorylation by binding to calcineurin.

9. The method according to claim 1, wherein said agent is FK506 or a synthetic mimetic thereof.

10. The method according to claim 1, wherein said agent is rapamycin or a synthetic mimetic thereof.

11. The method according to claim 1, wherein said agent is a cyclosporin.

12. The method according to claim 11, wherein said cyclosporin is cyclosporin A.

13. The method according to claim 12, wherein said cyclosporin is a synthetic derivative or mimetic of cyclosporin A.

14. The method according to claim 5, wherein said agent is FK506 or a synthetic mimetic thereof.

15. The method according to claim 5, wherein said agent is rapamycin or a synthetic mimetic thereof.

16. The method according to claim 5, wherein said agent is a cyclosporin.

17. The method according to claim 16, wherein Said cyclosporin is cyclosporin A.

18. The method according to claim 16, wherein said cyclosporin is a synthetic derivative or mimetic of cyclosporin A.

* * * * *

UNITED STATES PATENT AND TRADEMARK OFFICE
CERTIFICATE OF CORRECTION

PATENT NO. : 7,323,439 B2
APPLICATION NO. : 09/960708
DATED : January 29, 2008
INVENTOR(S) : Gerald R. Crabtree It is certified that error appears in the above-identified patent and that said Letters Patent is hereby corrected as shown below:

<u>Column 17:</u>

- Claim 1 line 42: Delete "anglogenesis" and replace it with --angiogenesis--.

<u>Column 18:</u>

- Claim 17 line 41: Delete "Said" and replace it with --said--.

Signed and Sealed this

Twenty-fourth Day of June, 2008

JON W. DUDAS
*Director of the United States Patent and Trademark Office*